United States Patent [19]
Hoffman

[11] Patent Number: 5,621,520
[45] Date of Patent: Apr. 15, 1997

[54] TRANSPARENCY INSPECTION METHOD FOR BLURRINESS IN VEHICLE WINDSCREENS WITH ELASTOMERIC LINERS

[75] Inventor: Joseph B. Hoffman, Nampa, Id.

[73] Assignee: Northrop Grumman Corporation, Los Angeles, Calif.

[21] Appl. No.: 644,442

[22] Filed: May 13, 1996

[51] Int. Cl.$^6$ ............................................. G01M 11/00
[52] U.S. Cl. .......................................................... 356/124.5
[58] Field of Search ............................ 356/445–448, 356/124, 124.5, 237; 250/201.9; 364/553, 524, 525; 283/115

[56] References Cited

U.S. PATENT DOCUMENTS

| | | |
|---|---|---|
| H220 | 2/1987 | Vogel . |
| 3,771,879 | 11/1973 | Chambu et al. . |
| 4,542,984 | 9/1985 | Shiota et al. . |
| 4,586,817 | 5/1986 | Ehemann, Jr. . |
| 4,641,963 | 2/1987 | Levine . |
| 4,653,909 | 3/1987 | Kuperman . |
| 4,776,692 | 10/1988 | Kalawsky . |

FOREIGN PATENT DOCUMENTS

| | | |
|---|---|---|
| 3600199 | 7/1986 | Germany . |
| 3522179 | 1/1987 | Germany . |
| 2027232 | 1/1990 | Japan . |

OTHER PUBLICATIONS

Erteza, Ahmed. 1976. "Sharpness Index and its Application to Focus Control." *Applied Optics* vol. 15, No. 4 (Apr. 1976): 877–881.

Barton, N.P. 1976. "The Use of Azimuth Scan MTF Techniques for the Evaluation of Optical Components and Systems." *SPIE* vol. 98 (Nov. 1976): 82–88.

Zhang, Y.W. and Cai, L.Z. 1984. "Point Spread and Transfer Functions for the Rainbow Holographic Process." *Applied Optics* vol. 23, No. 10 (May 15, 1984): 1493–1498.

Csorba, RCA Technical Notes, "Characterizing Contrast Transfer of a Device" Sep. 29, 1969 pp. 1–2.

*Primary Examiner*—K. Hantis
*Attorney, Agent, or Firm*—Terry J. Anderson; Karl J. Hoch, Jr.

[57] ABSTRACT

A method of determining the optical quality of blurriness in a windscreen transparency having a protective liner made of a particular material. A modulation transfer function (MTF) is measured through a clear transparency having a protective liner made of a particular material, resulting in measurements which are stored as a first data series. An MTF is measured through a degraded sample transparency having a protective liner made of the same particular material, resulting in measurements stored as a second data series. The first and second data series are combined to create a standard range template, which is stored in a data base record. An MTF is measured through an aircraft windscreen (a specimen transparency) having a protective liner made of the same particular material resulting in test measurements which are stored as a test data series. The first and second data series are plotted as target modulation versus target line frequency resulting in standard range template line plots of an acceptable range of optical quality of blurriness. The test data series are plotted as target modulation versus target line frequency resulting in a specimen line plot. The specimen line plot and the standard range template line plots are displayed in a single graph on a visual display. Using the displayed image, an operator schedules a time for replacement of the specimen depending upon the location of the specimen line plot relative to the standard range template line plots. If the specimen line plot is not within the standard range template line plots, replacement is done immediately.

23 Claims, 4 Drawing Sheets

TRANSPARENCY INSPECTION METHOD FOR BLURRINESS IN VEHICLE WINDSCREENS WITH ELASTOMERIC LINERS

FIELD OF THE INVENTION

The present invention is related to the field of measuring image resolution capability through transparencies, and more particularly to a method of testing the degree of degradation of a vehicle windscreen that has been coated with a protective elastomeric liner.

Modern aircraft use an elastomeric liner system to protect the outer surface of aircraft cockpit windscreen transparencies from abrasion.

The quality and serviceability of cockpit transparencies are critical problems with current systems. Transparency cross sections that utilize an external conductive coating in conjunction with a thin protective elastomeric liner introduce an additional optical element and potential defects. Since the elastomeric external liner is deformable, degradation in liner optics occurs with shipping, storage, installation, environmental exposure and routine maintenance. The liner material is subjected to optical degradation (called blurriness) from a variety of sources, such as improper covering, dust, sand, and other environmental conditions. Direct contact between the liner and other surfaces such as protective films and covers can transfer a surface deformation pattern to the liner. Although such a pattern may eventually "heal," the deformed liner may degrade optical performance of the windscreen for a significant period of time. Experience has shown that the liner surface deformation patterns are quite fine and result in "blurriness" when objects are viewed through the transparency.

With most transparencies, the scale of surface contour errors and variations in total thickness are generally of the order of the cross sectional thickness or greater. This leads to distortions which can be characterized with grid board inspection methods that are part of the transparency quality control test procedure. The small scale deformation pattern that can be introduced into the external liner surface, however, produces micro-distortions which cannot be characterized with standard inspection techniques. These micro-distortions appear to refract and scatter light thereby producing blurriness in objects viewed through the transparency.

Although there are objective, quantitative methods for measuring light transmission, haze, distortion and deviation there are no prior methods for measuring blurriness. Attempts to define and measure blurriness in the past have been limited to a subjective evaluation-by-committee process. A group of people, (pilots, engineers, etc.) look through the windscreen and vote as to whether the view is so degraded that replacement is necessary. This is costly and time consuming and the results are not consistent. These events indicated a strong need to design and develop a process and equipment to measure blurriness, to define a blurriness requirement, and to prepare a Quality Assurance (QA) inspection procedure.

It is therefore desirable to have an inspection method to identify and quantify liner optical degradation in the maintenance and serviceability of windscreen transparencies.

SUMMARY OF THE INVENTION

Briefly, the invention is concerned with a method and means of determining the optical quality of blurriness in a transparency having a protective liner made of a particular material. A modulation transfer function (MTF) is measured through a clear transparency having a protective liner made of the particular material, resulting in measurements which are stored as a first data series.

An MTF is measured through a degraded sample transparency having a protective liner made of the same particular material, resulting in measurements stored as a second data series. The first and second data series are combined to create a standard range template, which is stored in a data base record. An MTF is measured through a specimen transparency having a protective liner made of the same particular material resulting in test measurements which are stored as a test data series. The first and second data series are plotted as target modulation versus target line frequency resulting in standard range template line plots of an acceptable range of optical quality of blurriness. The test data series are plotted as target modulation versus target line frequency resulting in a specimen line plot. The specimen line plot and the standard range template line plots are displayed in a single graph on a visual display. Using the displayed image, an operator or a computer program schedules a time for replacement of the specimen depending upon the location of the specimen line plot relative to the standard range template line plots. If the specimen line plot is not within the standard range template line plots, replacement is done immediately.

The invention has the advantage that it provides a portable inspection method by which a qualitative determination can be made of a vehicle windscreen to determine if it has degraded to such a point that replacement is necessary.

An advantage of this image analysis method is that it measures real vision related effects that are experienced by an air crew.

Another advantage of this image analysis method is that the image quality measurements are very sensitive and can detect even slight degrees of blurriness.

Another advantage of this image analysis method is that video-based systems are very flexible and provide objective measures of optical quality.

DETAILED DESCRIPTION OF THE PREFERRED EMBODIMENTS

In an article by Bruce H. Walker published in Optics & Photronic News, May 1992, entitled "Update on the Modulation Transfer Function", the author defines a Modulation Transfer Function (MTF). The MTF of an optical system is a numerical and graphical representation of the ability of an optical system to produce an accurate image of an object. The author describes the method as follows. The MTF method assumes that an object being studied consists of a series of parallel black and white lines of constant high contrast and varying frequency. The image of such an object will be proportional in size, dependent on system magnification, and the contrast will vary between high (1.0) at zero frequency and 0.0 at some frequency equal to or less than the diffraction limit. The shape of the MTF curve plotted as amplitude versus frequency indicates the image quality of the optical system. Since the MTF format is concise and easily understood, the method has become widely used for the specification and measurement of image quality.

An OPTIMA System from OPTICS 1 Inc. of Westlake Village, Calif. is a video based MTF measurement system that includes an image processing board, software, manual, Sony CCD camera, IBM PC compatible with 486 processor, VGA monitor, 2 inch aperture collimator, optical rail with support mounts, 20× and 40× microscope objectives, microscope focusing hardware, and C-mount adapter. A standard microscope body and objective lens mounts directly to a charge-coupled device (CCD) video camera. Displayed on the monitor is a real-time video graph display of a computed MTF plotted as modulation versus frequency. The system is supplied with an Air Force USAF 1951 resolution target that can be used as a test object, resulting in square wave MTF data. Alternatively, an illuminated slit may be used as a test object, resulting in sine wave MTF data.

An image processing system board in the OPTIMA System, Model 1000 from Optics 1, Inc. runs on a 485 IBM compatible personal computer, equipped with Windows 3.1, and displayed on a VGA Monitor with RS-70 capability.

Aligned Target/Imaging System

Figure 1:
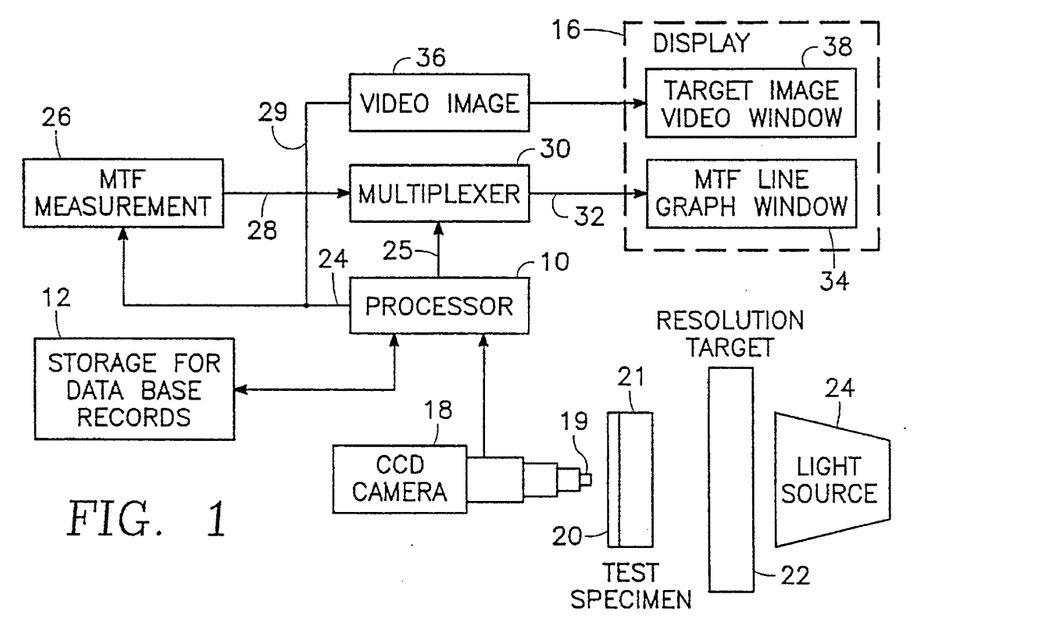
FIG. 1 is an overall view of a first embodiment of a video-based testing apparatus of the present invention.
Figure 7:
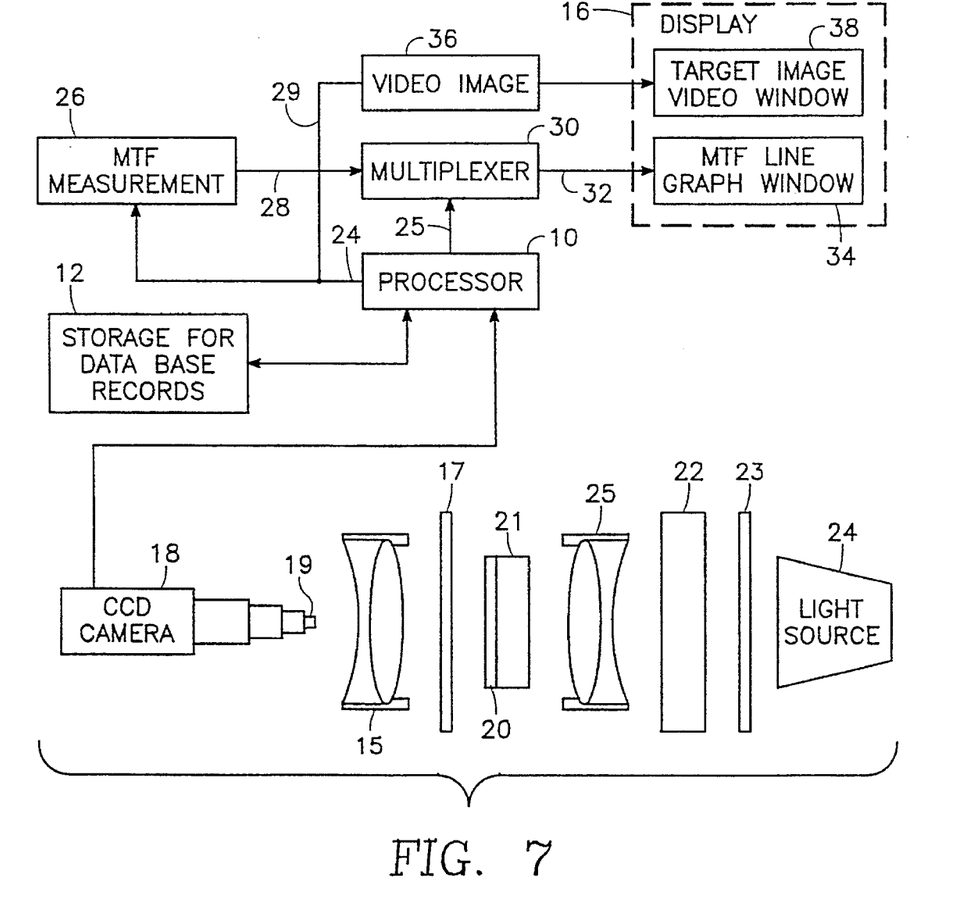
FIG. 7 is an overall view of a second embodiment of a video-based testing apparatus of the present invention.

Refer now to FIG. 1 which is an overall view of a first embodiment of a video-based testing apparatus of the present invention. A processor (10) is connected to a storage (12) used for storing data base records and a display (16). A charged coupled device (CCD) camera is connected as an input device to the processor (10). The CCD camera (18) may be a Sony Model #XC-75 CCD Camera. The CCD camera is fitted with a microscope lens (19). A test specimen (21) that has a thin elastomeric liner (20) is placed in front of the lens (19). On an opposite side of the test specimen is a resolution target (22) which may be either a USAF 1951 Negative Chromium or a precision mounted air slit (25 um), both of which can be obtained from Melles Griot, 1770 Kettering Street, Irvine Calif. A light source (24) is placed to shine through the resolution target (22). The light source (24) may be a 150 watt fiber optic illuminator manufactured by Dolan-Jenner, model #180, or a slide projector. For bar target measurements, a diffuse light source is required. Therefore, the light guide output must b expanded with a collimator probe or separate collimating lens, such as shown in FIG. 7.

A CCD camera output (24) is connected to MTF measurement logic (26) and to a video image logic (36) that causes a target video image (29) captured by the CCD camera to be displayed in a target image video window (38). A specimen line plot (28) output from the MTF measurement logic (26) is connected to an input of a multiplexer (30). Another input of multiplexer (30) is connected to standard range template line plots output (25) from the processor (10). The multiplexer (30) combines the two inputs (25, 28) to produce single graph output (32) that is displayed in an MTF line graph window (34) on display (16).

Figure 2:
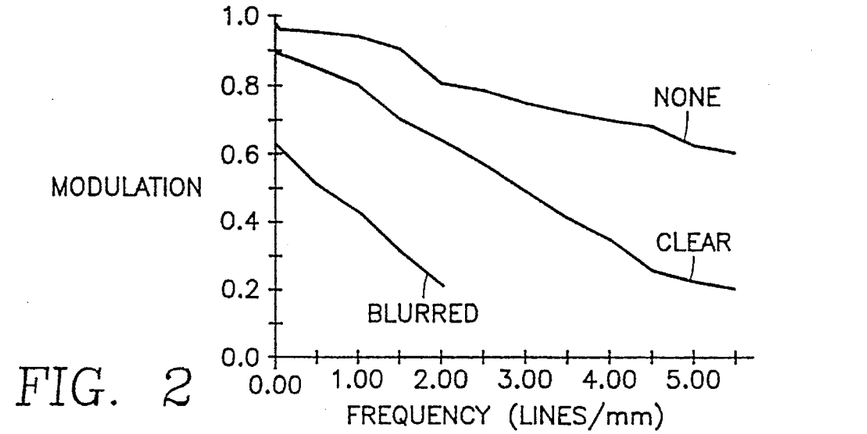
FIG. 2 is a chart of a plot of a standard range template in accordance with the present invention.

Refer to FIG. 2 which is a chart of a plot of a standard range template in accordance with the present invention. This template is produced by first recording MTF measurements taken without a transparency in front of the CCD camera lens. This produces a first data series plotted and labeled "NONE" in FIG. 2. Next MTF measurements are recorded taken with a clear transparency in front of the CCD camera lens. This produces a second data series plotted and labeled "CLEAR" in FIG. 2. Finally MTF measurements are recorded taken with a blurred and unacceptable transparency in front of the CCD camera lens. This produces a third data series plotted and labeled "BLURRED" in FIG. 2.

A blurred and unacceptable transparency provides a standard of blurrines against which a test specimen is compared for acceptance or rejection. This standard is obtained, for example, by taking and averaging measurements of several transparencies that have been designated as unacceptable by a committee. The committee may be, for example, a group of pilots, engineers, etc. who look through each windscreen and vote as to whether the view is so degraded that replacement is necessary. The data series obtained by the three measurements described above are stored in a data base record in the storage (12) as a standard range template.

Figure 3:
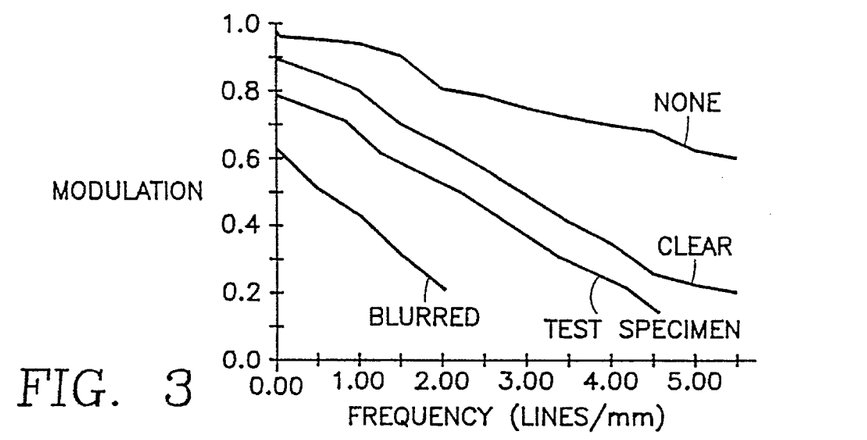
FIG. 3 is a chart of a plot of a test specimen that is within the standard range template of FIG. 2.

Refer to FIG. 3 which is a chart of a plot of a test specimen that is within the standard range template of FIG. 2. This chart is obtained by placing a test specimen, such as an installed aircraft windscreen between the microscope lens (19) and the resolution target (22). For an installed windscreen this means that the light source (24) and target (22) are placed within the cockpit and the CCD camera (18) is placed outside the cockpit at the surface of the exterior of the windscreen. An image of the target captured by the CCD camera is aligned such that it fills a specified area of the target image window (38) on display (16). An MTF measurement is made resulting in a test data series.

The standard range template is called up from the data base record stored in storage (12) and is combined with the test data series in a single graph that is displayed in MTF line graph window (34) on display (16). The graph appears as in FIG. 3. The solid line is the test specimen plot that is within the range of clear and blurred and the user designated this windscreen as not needing replacement. Future replacement time can be estimated by noting the location of the test specimen line plot with reference to the lower line plot for a blurred window.

It should be understood that because the microscope lens can only sample a small area of the windscreen specimen being tested, several areas of the windscreen should be tested to insure that a degraded area is not localized, resulting in missing replacement that may have been necessary.

Figure 4:
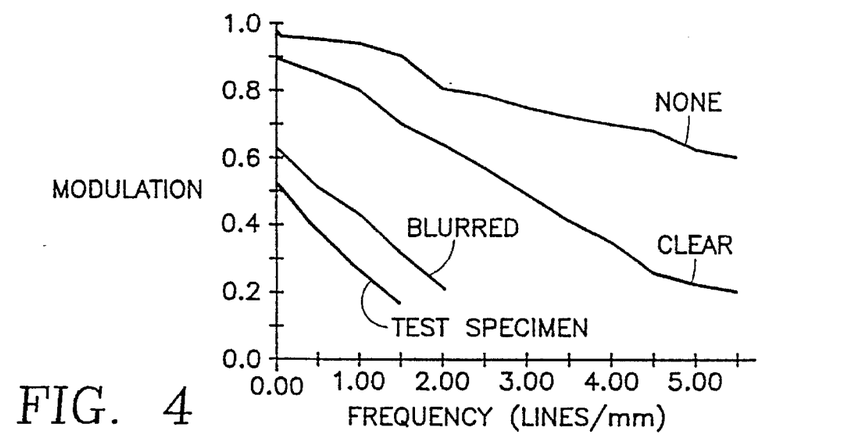
FIG. 4 is a chart of a plot of a test specimen that is outside the standard range template of FIG. 2.

Refer to FIG. 4 which is a chart of a plot of a test specimen that is outside the standard range template of FIG. 2. This chart is obtained by placing a test specimen, such as an installed aircraft windscreen between the microscope lens (19) and the resolution target (22). For an installed windscreen this means that the light source (24), target (22) are placed within the cockpit and the CCD camera (18) is place outside the cockpit. An image of the target captured by the CCD camera is aligned such that it fills a specified area of the target image window (38) on display (16). An MTF measurement is made resulting in a test data series. The standard range template is called up from the data base record stored in storage (12) and is combined with the test data series in a single graph that is displayed in MTF line graph window (34) on display (16). The graph appears as in FIG. 4. The solid line is the test specimen plot that is outside the range of clear and blurred and the user designates this windscreen as needing replacement immediately.

It should be understood that because the microscope lens can only sample a small area of the windscreen specimen being tested, several areas of the windscreen should be tested to insure that a degraded area is not localized, resulting in making a replacement that may not have been necessary.

Calibration Method Flow Chart

Figure 5:
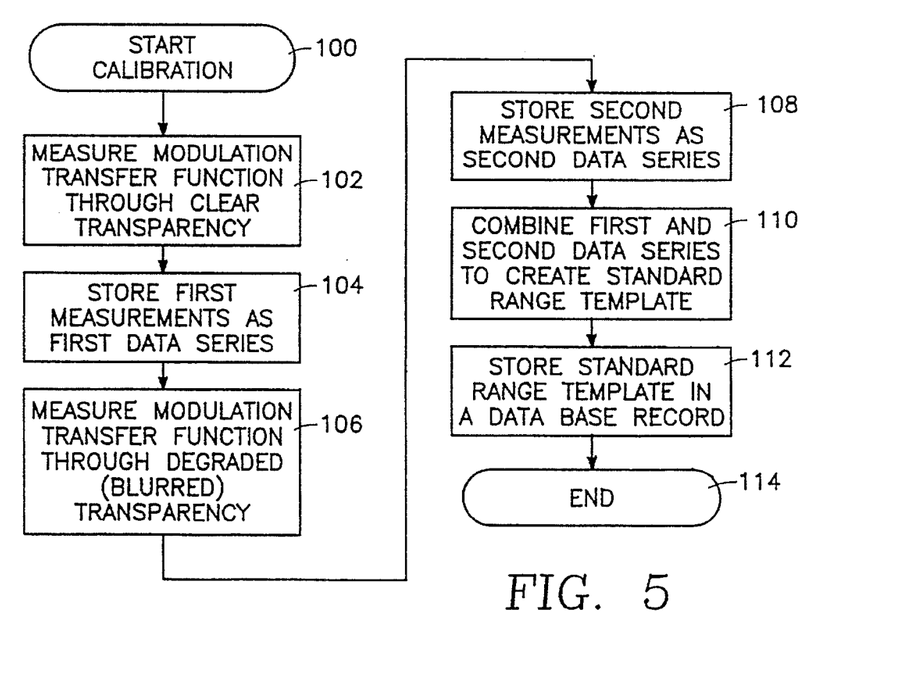
FIG. 5 is flow chart of a calibration method of the present invention.

Refer to FIG. 5 which is flow chart of a calibration method of the present invention. The method begins (100). A modulation transfer function (MTF) is measured (102) through a clear transparency having a protective liner made of the particular material, resulting in first measurements. The first measurements are stored (104) as a first data series. A modulation transfer function (MTF) is measured (106) through a degraded sample transparency having a protective liner made of the particular material, resulting in second measurements. The second measurements are stored (108) as a second data series. The first and second data series are combined (110) to create a standard range template. The standard range template is stored (112) in a data base record and the calibration ends (114).

Test Method Flow Chart

Figure 6:
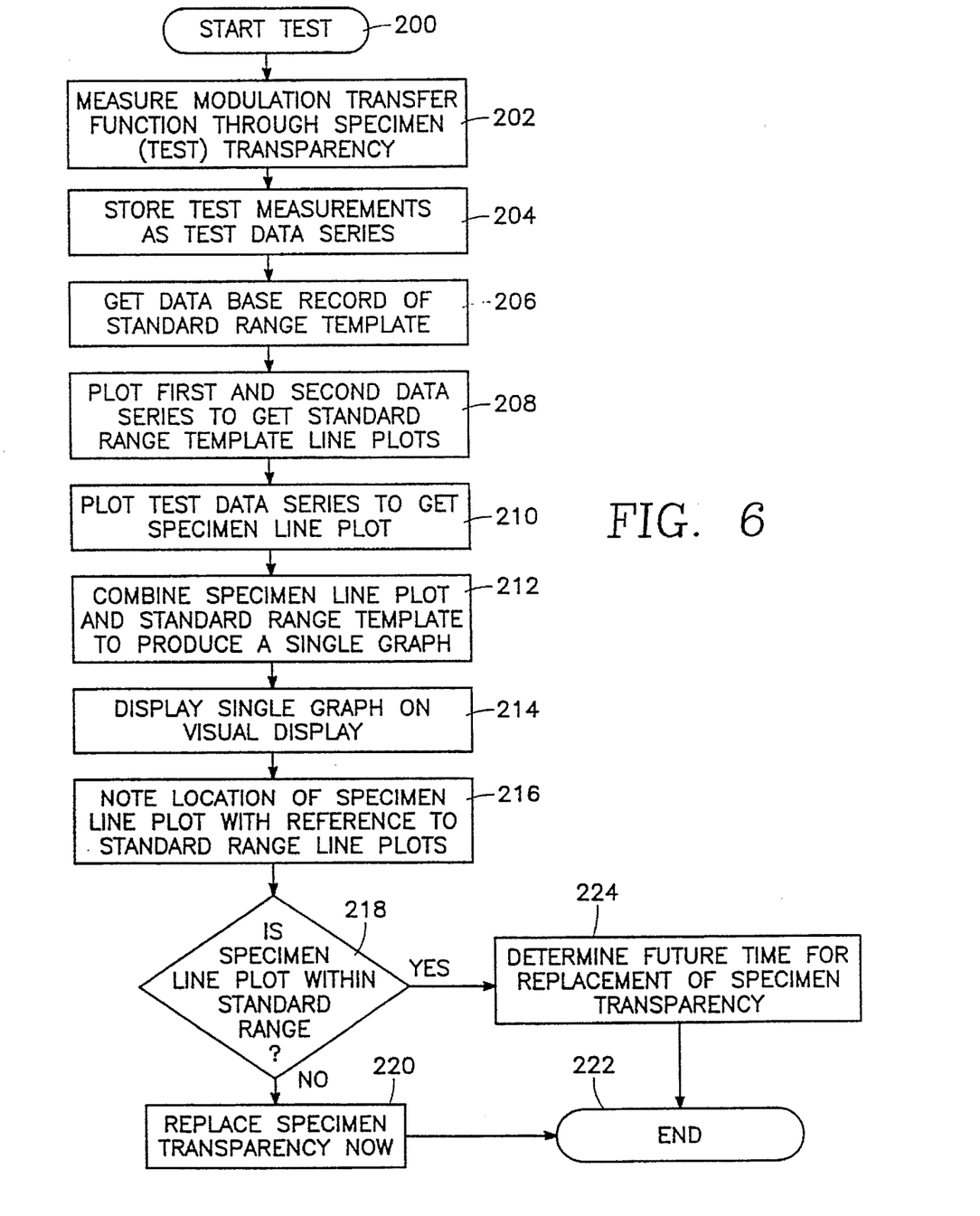
FIG. 6 is flow chart of a test method of the present invention.

Refer to FIG. 6 is flow chart of a test method of the present invention. The test starts (200). A modulation transfer function (MTF) is measured (202) through a specimen transparency having a protective liner made of the same particular material used in calibration resulting in test measurements. The test measurements are stored (204) in a test record as a test data series. The first and second data series are plotted (208) as target modulation versus target line frequency resulting in standard range template line plots of an acceptable range of optical quality of blurriness for a transparency having a protective liner made of the particular material. The test data series are plotted as target modulation versus target line frequency resulting in a specimen line plot. The specimen line plot and the standard range template line plots are combined (214) in a single graph. The single graph is displayed (214) on a visual display.

A user notes the location of the specimen line plot with reference to the standard range line plots (216). If the specimen line plot is within the standard range (218), the user schedules a time for replacement of the specimen depending upon a location of the specimen line plot relative to the standard range template line plots (224).

Alternatively, a computer logic or software program subtracts each data point of the standard template data series from the corresponding data point of test specimen data series. If all positive numbers result, the specimen line plot is within the standard range (218). The a computer program schedules a time for replacement of the specimen depending upon the numerical values obtained which indicates a location of the specimen line plot relative to the standard range template line plots (224).

If all negative numbers result, the specimen line plot is outside the standard range (218). The computer program or logic designates the specimen transparency for replacement.

Projected Target System

A projected target embodiment of the invention is shown in FIG. 7. Elements of FIG. 7 that are identical to corresponding elements of FIG. 1 have the same reference numerals, and a description thereof will not be repeated. In this configuration, a 3-bar target (22) is projected on a screen, which could be done by placing the target in a standard photographic slide projector or the fiber optic illuminator described above with reference to FIG. 1. The light source (24) shines through a diffuser (23) and through the resolution target (22). A collimating lens (25) focuses parallel rays through the test specimen (21) and onto a translucent screen (17), which may be ground glass. The field lens (17) and video system then image the target on the back side of the screen (15). The final image size and hence the line spacing is a function of the magnification of both the projection and video imaging systems. Measurements made with this configuration may not be as satisfactory as in the first embodiment described above because of the coarseness of the screen.

Reflected Target Configuration

A reflected target configuration may be desirable where space within a cockpit is limited. The optical path is similar to the projected target embodiment shown in FIG. 7. A mirror is placed inside the cockpit and the light source and projector lenses and CCD camera are placed on the same side of the windscreen. The optical path then includes the mirror from which the target image is reflected. This is of particular interest since the target projection hardware and the components for the video imaging system can be positioned side-by-side outside the aircraft. Thus, the only other optical component required over that shown in FIG. 7 is an adjustable mirror.

An advantage of this system is increased sensitivity. Since, for a full scale transparency, the target image would take two passes though the transparency, image degradation could be enhanced for any particular level of blurring. Also, by properly positioning the mirror and transparency it is possible to separate the image spots on the transparency by the nominal eye separation distance; thus, simulating a combined effect experienced by a human observer. Since the only component that is required on the opposite side of the test article is an optical quality mirror, a reflected target configuration has potential application as a basis for a maintenance test method for installed transparencies. A reflected target configuration provides results that are consistent with the aligned target configuration.

While the invention has been particularly shown and described with reference to preferred embodiments thereof, it will be understood by those skilled in the art that the foregoing and other changes in form and detail may be made therein without departing from the scope of the invention.

What is claimed is:

1. A method of determining optical quality of blurriness in a windscreen transparency having a protective liner made of a particular material comprising steps of:

measuring a modulation transfer function (MTF) through a clear transparency having a protective liner made of said particular material, resulting in first measurements;

storing said first measurements as a first data series;

measuring a modulation transfer function (MTF) through a degraded sample transparency having a protective liner made of said particular material, resulting in second measurements;

storing said second measurements as a second data series;

combining said first and second data series to create a standard range template;

storing said standard range template in a data base record;

measuring a modulation transfer function (MTF) through a specimen transparency having a protective liner made of said particular material resulting in test measurements;

storing said test measurements in a test record as a test data series;

plotting said first and second data series as target modulation versus target line frequency resulting in standard range template line plots of an acceptable range of optical quality of blurriness for a transparency having a protective liner made of said particular material;

plotting said test data series as target modulation versus target line frequency resulting in a specimen line plot; and combining said specimen line plot and said standard range template line plots in a single graph.

2. The method in accordance with claim 1 comprising a further step of:

scheduling a time for replacement of said specimen depending upon a location of said specimen line plot relative to said standard range template line plots.

3. The method in accordance with claim 2 wherein said scheduling step comprises steps of:

subtracting each data point of said standard template data series from a corresponding data point of said test specimen data series; and, scheduling a time for replacement of said specimen depending upon numerical values obtained, said values indicating a location of said specimen line plot relative to said standard range template line plots.

4. The method in accordance with claim 1 comprising a further step of:

designating for replacement said specimen transparency upon a condition that said specimen line plot is not within said standard range template line plots.

5. The method in accordance with claim 4 wherein said designating step comprises steps of:

subtracting each data point of said standard template data series from a corresponding data point of said test specimen data series; and, designating for replacement said specimen transparency upon a condition that all negative numbers result, indicating said specimen line plot is not within said standard range template line plots.

6. The method in accordance with claim 1 wherein said step of measuring a modulation transfer function (MTF) through a specimen transparency having a protective liner made of said particular material resulting in test measurements comprises further steps of:

placing a measuring device on a side of said transparency having said protective liner;

placing a resolution target on an opposite side of said transparency; and, projecting an image of said resolution target into said measuring device.

7. The method in accordance with claim 1 wherein said step of measuring a modulation transfer function (MTF) through a specimen transparency having a protective liner made of said particular material resulting in test measurements comprises further steps of:

placing a mirror on a side of said transparency having said protective liner;

placing a measuring device and a resolution target on an opposite side of said transparency; and, projecting an image of said resolution target onto said mirror so that said image is reflected into said measuring device.

8. An apparatus for determining optical quality of blurriness in a windscreen transparency having a protective liner made of a particular material comprising:

processing means for processing data;

measurement means including first measuring means for measuring a modulation transfer function (MTF) through a clear transparency having a protective liner made of said particular material, resulting in first measurements;

said measurement means including second measuring means for measuring a modulation transfer function (MTF) through a degraded sample transparency having a protective liner made of said particular material, resulting in second measurements;

storage means connected to said processing means for storing said first measurements as a first data series and said second measurements as a second data series;

said processing means including first combining means for combining said first and second data series to create a standard range template;

said processing means storing said standard range template in a data base record in said storing means;

said processing means including third measuring means for measuring a modulation transfer function (MTF) through a specimen transparency having a protective liner made of said particular material resulting in test measurements;

said processing means storing said test measurements in a test record as a test data series in said storing means;

said processing means including first plotting means for plotting said first and second data series as target modulation versus target line frequency resulting in standard range template line plots of an acceptable range of optical quality of blurriness for a transparency having a protective liner made of said particular material;

said measurement means including second plotting means for plotting said test data series as target modulation versus target line frequency resulting in a specimen line plot; and second combining means connected to said measurement means and to said processor for combining said specimen line plot and said standard range template line plots in a single graph.

9. The apparatus in accordance with claim 8 further comprising:

scheduling means for scheduling a time for replacement of said specimen depending upon a location of said specimen line plot relative to said standard range template line plots.

10. The apparatus in accordance with claim 9 wherein said scheduling means comprises:

subtracting means for subtracting each data point of said standard template data series from a corresponding data point of said test specimen data series;

said scheduling means scheduling a time for replacement of said specimen depending upon numerical values obtained, said values indicating a location of said specimen line plot relative to said standard range template line plots.

11. The apparatus in accordance with claim 8 further comprising:

designating means for designating for replacement said specimen transparency upon a condition that said specimen line plot is not within said standard range template line plots.

12. The apparatus in accordance with claim 11 wherein said designating means comprises:

subtracting means for subtracting each data point of said standard template data series from a corresponding data point of said test specimen data series;

said designating means designating for replacement said specimen transparency upon a condition that all negative numbers result, indicating said specimen line plot is not within said standard range template line plots.

13. The apparatus in accordance with claim 8 wherein said measurement means comprises:

an imaging camera fitted with a microscope lens placed on a side of said transparency having said protective liner;

a target on an opposite side of said transparency; and, a light source located such that said target is illuminated.

14. The apparatus in accordance with claim 8 wherein said measurement means comprises:

an imaging camera placed on a side of said transparency having said protective liner;

a translucent screen on an opposite side of said transparency; and, projection means for projecting a target onto said screen.

15. The apparatus in accordance with claim 8 wherein said measurement logic connected to said processor comprises:

an imaging camera placed on a side of said transparency having said protective liner;

a translucent screen on an opposite side of said transparency;

a target; and, a projector;

said target and said projector being positioned such that said target is projected onto said screen.

16. The apparatus in accordance with claim 8 wherein said measurement means comprises:

reflecting means placed on a side of said transparency having said protective liner;

an imaging camera placed on an opposite side of said transparency;

a translucent screen placed on said opposite side of said transparency; and, projection means for projecting a target onto said screen;

said imaging camera, said translucent screen, and said projection means being positioned with respect to each other such that an image of said target projected onto said screen is reflected into said imaging camera.

17. The apparatus in accordance with claim 8 wherein said measurement logic connected to said processor comprises:

a mirror placed on a side of said transparency having said protective liner;

an imaging camera placed on an opposite side of said transparency;

a translucent screen placed on said opposite side of said transparency;

a target; and, a projector;

said imaging camera, said translucent screen, said target and said projector being positioned with respect to each other such that an image of said target projected onto said screen is reflected into said imaging camera.

18. An apparatus for determining optical quality of blurriness in a windscreen transparency having a protective liner made of a particular material comprising:

a processor;

a measurement logic connected to said processor;

said measurement logic including a first measuring logic that measures a modulation transfer function (MTF) through a clear transparency having a protective liner made of said particular material, resulting in first measurements;

said measurement logic including a second measuring logic that measures a modulation transfer function (MTF) through a degraded sample transparency having a protective liner made of said particular material, resulting in second measurements;

a storage connected to said processing logic that stores said first measurements as a first data series and said second measurements as a second data series;

said processor including first combining logic that combines said first and second data series to create a standard range template;

said processor storing said standard range template in a data base record in said storage;

said processor including third measuring logic that measures a modulation transfer function (MTF) through a specimen transparency having a protective liner made of said particular material resulting in test measurements;

said test measurements being stored in said storage in a test record as a test data series;

said processor including first plotting logic that plots said first and second data series as target modulation versus target line frequency resulting in standard range template line plots of an acceptable range of optical quality of blurriness for a transparency having a protective liner made of said particular material;

said measurement logic including second plotting logic that plots said test data series as target modulation versus target line frequency resulting in a specimen line plot; and a multiplexer connected to said measurement logic and to said processor that combines said specimen line plot and said standard range template line plots in a single graph.

19. The apparatus in accordance with claim 18 further comprising:

scheduling logic that schedules a time for replacement of said specimen depending upon a location of said specimen line plot relative to said standard range template line plots.

20. The apparatus in accordance with claim 19 wherein said scheduling logic comprises:

a subtracting logic that subtracts each data point of said standard template data series from a corresponding data point of said test specimen data series;

said scheduling logic scheduling a time for replacement of said specimen depending upon numerical values obtained, said values indicating a location of said specimen line plot relative to said standard range template line plots.

21. The apparatus in accordance with claim 18 further comprising:

designating logic that designates for replacement said specimen transparency upon a condition that said specimen line plot is not within said standard range template line plots.

22. The apparatus in accordance with claim 21 wherein said designating logic comprises:

a subtracting logic that subtracts each data point of said standard template data series from a corresponding data point of said test specimen data series;

said designating logic designating for replacement said specimen transparency upon a condition that all negative numbers result, indicating said specimen line plot is not within said standard range template line plots.

23. The apparatus in accordance with claim 18 wherein said measurement logic connected to said processor comprises:

an imaging camera fitted with a microscope lens placed on a side of said transparency having said protective liner;

a target on an opposite side of said transparency; and, a light source located such that said target is illuminated.

* * * * *